(12) United States Patent
Scholz et al.

(10) Patent No.: US 7,876,946 B2
(45) Date of Patent: Jan. 25, 2011

(54) METHOD FOR CORRECTING TRUNCATION ARTIFACTS

(75) Inventors: Bernhard Scholz, Heroldsbach (DE); Ernst-Peter Rühmschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 971 days.

(21) Appl. No.: 11/729,526

(22) Filed: Mar. 29, 2007

(65) Prior Publication Data
US 2007/0230652 A1 Oct. 4, 2007

(30) Foreign Application Priority Data
Mar. 29, 2006 (DE) .................. 10 2006 014 630

(51) Int. Cl.
*G06K 9/00* (2006.01)
(52) U.S. Cl. ..................................... 382/131
(58) Field of Classification Search ................. 382/128, 382/131; 378/4, 21
See application file for complete search history.

(56) References Cited

U.S. PATENT DOCUMENTS

| | | | |
|---|---|---|---|
| 6,307,909 B1 | 10/2001 | Flohr et al. | |
| 6,339,223 B1 * | 1/2002 | Motomura et al. | 250/363.07 |
| 6,810,102 B2 | 10/2004 | Hsieh et al. | |
| 6,856,666 B2 * | 2/2005 | Lonn et al. | 378/8 |
| 6,983,034 B2 * | 1/2006 | Wang et al. | 378/4 |
| 2006/0222144 A1 * | 10/2006 | Russinger | 378/16 |
| 2007/0131858 A1 * | 6/2007 | Wollenweber et al. | 250/252.1 |
| 2007/0195923 A1 * | 8/2007 | Netsch et al. | 378/4 |

FOREIGN PATENT DOCUMENTS

| DE | 198 54 917 A1 | 6/2000 |
|---|---|---|
| DE | 103 45 705 A1 | 9/2004 |

OTHER PUBLICATIONS

J. Hsieh, E. Chao, J. Thibault, B. Grekowicz, A. Horst, S. McOlash and T.J. Myers; "A novel reconstruction algorithm to extend the CT scan field-of-view"; Medical Physics 31; Sep. 2004; pp. 2385-2391; vol. 31, No. 9.

(Continued)

*Primary Examiner*—Bhavesh M Mehta
*Assistant Examiner*—Shervin Nakhjavan

(57) ABSTRACT

A method is claimed for correcting truncation artifacts in a tomography method, wherein internal checkpoints having a low level of attenuation are selected within the projection image and external checkpoints are defined by extrapolation based on the internal checkpoints. An adaptation function is then tailored to the internal checkpoints and the external checkpoints. This allows truncation artifacts to be effectively suppressed during the reconstruction of sectional images.

19 Claims, 4 Drawing Sheets

OTHER PUBLICATIONS

Ohnesorge B et al., "Efficient correction for CT image artifacts caused by objects extending outside the scan field of view", Medical Physics, Jan. 2000, pp. 39-46, vol. 27.

Penβel C et al., "Hybrid Detruncation Algorithm for the Reconstruction of CT data", RSNA-Article 2004, pp. 1-18.

Starman J et al., "Extrapolating Truncated Projections Using $0^{th}$ and $1^{st}$ Moment Constraints", Scientific Papers, Code: SSA17-08, Session Physics (CT Reconstruction), RSNA 2004, pp. 1-2; Abstract pp. 1-2.

Lewis et al., "The treatment of atmospheric dispersion data in the presence of noise and baseline drift", Boundary Layer Meteorol, 1995, pp. 53-85, vol. 72, Kluwer Academic Publishers, Netherlands.

Sourbelle et al., "Reconstruction from truncated projections in cone-beam CT using adaptive detruncation", Paper #1506, RSNA 2003.

K. Sourbelle, M. Kachelriess, W.A. Kalender, Reconstruction from truncated projections in CT using adaptive detruncation:, Journal European Radiology, May 2005, pp. 1008-1014, vol. 15.

* cited by examiner

METHOD FOR CORRECTING TRUNCATION ARTIFACTS

CROSS REFERENCE TO RELATED APPLICATIONS

This application claims priority of German application No. 1 014 630.1 filed Mar. 29, 2006, which is incorporated by reference herein in its entirety.

FIELD OF THE INVENTION

The invention relates to a method for correcting truncation artifacts in a tomography method and a device for performing the tomographic process on an object under examination.

BACKGROUND OF THE INVENTION

Such a method is known from HSIEH, J. et al., "A novel reconstruction algorithm to extend the CT scan field-of-view", MED. PHYS. 31 (9), September 2004, pages 2385 to 2391. With the known method truncation artifacts can be suppressed but then appear when the object to be examined extends into regions outside what is known as the measuring field region. The resulting projection images are referred to as cut off or truncated. Truncated projection images produce artifacts when the sectional images are reconstructed. In particular the image values close to the edges in the sectional images are generally too high and in a central region they are too low. The sectional images affected by truncation artifacts are therefore of only limited value for diagnosis purposes.

With the known method an equivalent body is constructed in the peripheral region of a projection image, when there is attenuation there, to produce the same attenuation as the object to be examined in the peripheral region. The equivalent body is then projected onto the region outside the projection image using parallel beam geometry. This means that the projection image is continued in a region outside the projection image.

The projection of the equivalent body using parallel beam geometry onto the region outside the projection image requires the fan beam data recorded using fan beam geometry to be converted to parallel beam data. Conversion of the fan beam data to parallel beam data is also referred to as rebinning. What is known as rebinning is computation-intensive and cannot be used in all instances. With computed tomography recordings with C-arm systems in particular the waiting and computation times required for rebinning are not available due to the reconstruction times, which are in any case very long.

SUMMARY OF THE INVENTION

Based on this prior art, the object of the invention is therefore to specify a method for correcting truncation artifacts that is improved with regard to the reduction of truncation artifacts and that can be implemented with comparatively little computation outlay.

This object is achieved by a method with the features of the independent claim. Advantageous embodiments and developments are set out in the dependent claims.

For the method, wherein:
radiation is emitted by a radiation source and the emitted radiation is used to irradiate an object to be examined in different projection directions,
the radiation penetrating the object to be examined is detected by a detector and
projection images recorded by the detector are extended by extrapolation.

With the method a plurality of checkpoints, having a low level of attenuation compared with adjacent points, are selected within the projection image and the extrapolation is carried out as a function of the selected checkpoints. The selection of low-attenuation checkpoints ensures that the extrapolated values decrease in an outward direction. This is because the low-attenuation image points are those containing no or little structural information. It is therefore not possible for structural information contained at the edge of the projection image to influence significantly or even falsify the extrapolation.

It has proven that truncation artifacts can be effectively suppressed using such a method. At the same time the computation outlay is kept within limits, as out of the large number of image points only a limited number of checkpoints are used to carry out the extrapolation.

With a preferred embodiment of the method, the checkpoints are selected by defining local extreme values within the projection image, showing a relatively low level of attenuation of the radiation through the object to be examined. Selecting local extreme values means that checkpoints are selected, which contain little structural information. It can therefore be expected that extrapolation of the checkpoints to regions outside the projection image will give realistic results.

In order to suppress noise effects and the impact of small-scale structures in the object to be examined, the selected checkpoints can be subjected to a smoothing method. A sliding mean value of the selected checkpoints can for example be calculated with such a method.

The checkpoints can be extrapolated by defining external checkpoints by extrapolation based on the internal checkpoints selected within the projection image, the projection values of said external checkpoints decreasing monotonously in an outward direction. This procedure has the advantage that only a little computation outlay is required to carry out the extrapolation.

The extrapolated external checkpoints can also be weighted with a monotonously decreasing profile function, to achieve a smooth pattern for the external checkpoints, in particular to achieve a smooth run-out of the external checkpoints.

The intermediate values between the external checkpoints can ultimately be calculated by tailoring an adaptation curve to the internal and external checkpoints. This means that the projection image can be continued into the regions outside the projection image according to the resolution within the projection image.

The computation outlay for calculating the intermediate values can be further reduced, if gradual linear interpolation is carried out between the checkpoints outside the projection image. There is then no need to adjust an overall curve.

BRIEF DESCRIPTION OF THE DRAWINGS

Further characteristics and advantages of the invention will emerge from the description which follows, in which exemplary embodiments of the invention are described in detail with reference to the accompanying drawing, in which.

DETAILED DESCRIPTION OF THE INVENTION

Figure 1:
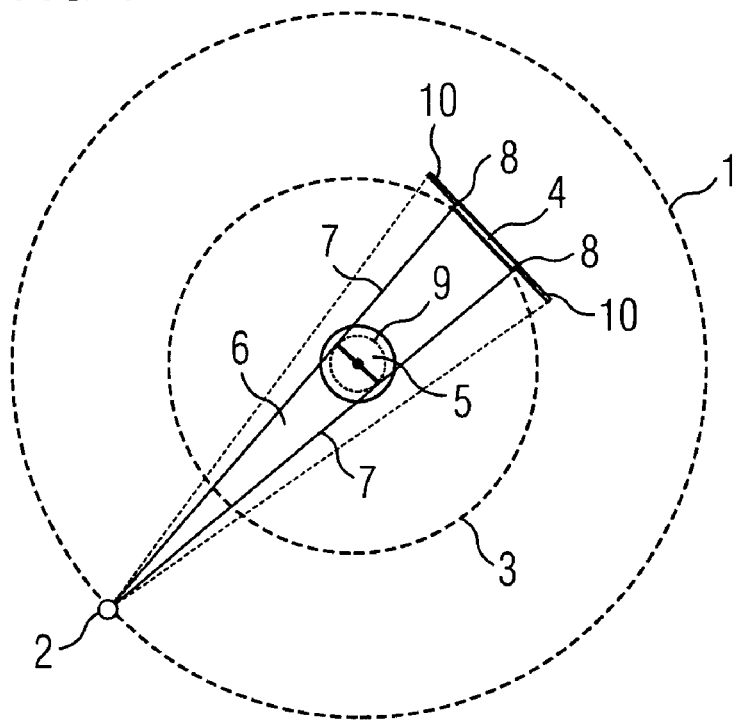
FIG. 1 shows a view of the path of a detector and a radiation source around an object to be examined, viewed axially.

FIG. 1 shows an axial top view of a peripheral path 1 of an x-ray radiation source 2 and a peripheral path 3 of an x-ray detector 4 around an object to be examined 5. The x-ray detector 4 is preferably a digital flat image detector or a flat-panel detector. The object to be examined 5 can be an animal or human body for example.

The x-ray radiation source 2 emits a beam fan 6 from a beam focus, the peripheral beams 7 of said beam fan 6 striking edges 8 of the x-ray detector 4.

The x-ray radiation source 2 and the x-ray detector 4 respectively travel around the object 5 in such a manner that the x-ray radiation source 2 and the x-ray detector 4 face each other on opposite sides of the object 5. During the common movement of the x-ray detector 4 and x-ray radiation source 2 the peripheral beams 7 of the beam fan 6 define a measuring field circle 9, which lies partially or even completely within the object to be examined 5 when the scale of the object 5 is too large. The regions of the object 5 lying outside the measuring field circle 9 are therefore not mapped onto the x-ray detector 4. In some circumstances therefore the x-ray detector 4 records truncated projection images of the object 5. Sectional images of the object to be examined 5 are reconstructed from the truncated projection images by an evaluation unit (not shown in the diagram), which is connected downstream of the x-ray detector 4. During the reconstruction of sectional images of the irradiated object 5 located in the fan plane 6, the truncated projection images result in truncation artifacts. In particular image values of the reconstructed sectional image in the peripheral regions are too high, while the image values within the sectional image are too low. Even if the object to be examined 5 attenuates the beams of the beam fan from the x-ray radiation source in a regular manner, an image value profile running in a perpendicular manner across the sectional image therefore exhibits a rather dish-shaped pattern.

Too high image values signify that too high a level of attenuation of the x-ray radiation emitted by the x-ray radiation source 2 through the object 5 is shown in the reconstructed sectional image, while too low image values show too low a level of attenuation through the object 5.

To reduce the incidence of truncation artifacts in the reconstructed sectional image, the recorded projection image at the edges 8 of the x-ray detector 4 is extrapolated to an extended detector surface 10. The reconstruction is then carried out based on the supplemented projection images. It is thus possible to suppress truncation artifacts in the reconstructed sectional image in an effective manner.

This is described in more detail with reference to the object 5 shown in FIG. 2.

Figure 2:
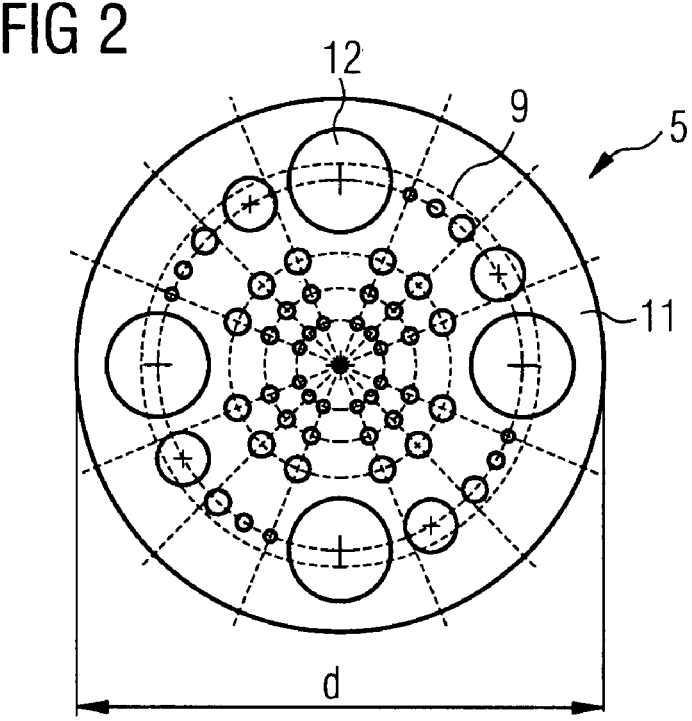
FIG. 2 shows a cross-sectional view of a phantom body used to verify the imaging quality, viewed axially.

The diagram of the object 5 shown in FIG. 2 is a cross-section through a phantom body 11, which can be used to investigate computed tomography devices. The phantom body 11 has three different contrast layers, each having inserts 12 of different density. A low contrast layer has inserts 12 with the values 3 HU, 5 HU, 10 HU and 15 HU. A medium contrast layer has inserts 12 with densities of 20 HU, 25 HU, 30 HU and 40 HU. The external diameter d of the phantom body 11 is dimensioned such that the outer inserts 12 lie partially outside the measuring field circle 9.

Figure 3:
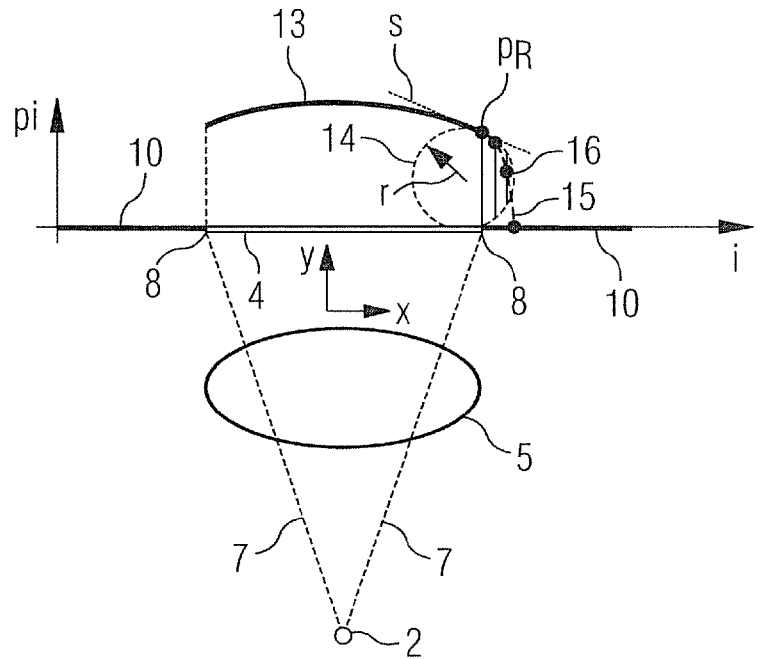
FIG. 3 shows a diagram of a correction method for suppressing artifacts according to the prior art.

FIG. 3 shows an extrapolation method according to the prior art.

The radiation from the focus of the x-ray radiation source 2 penetrates the object to be examined 5 and strikes the x-ray detector 4. The x-ray detector 4 uses detector elements in a line indexed with the column index i to detect projection values $p_i$, which form a projection value profile 13 between the edges 8 of the x-ray detector 4 in the line direction.

To extrapolate the projection value profile 13 to the extended detector surface 10 in the line direction, a water cylinder 14 is defined at the edge 8 of the x-ray detector 4, producing the same attenuation in each instance at the edges 8 using parallel beam geometry, as the object 5 in the region of the peripheral beam 7. Since parallel beam geometry is assumed, the location of the water cylinder 14 in beam direction y is irrelevant.

The midpoint position x of the water cylinder 14 perpendicular to the beam direction y and the radius r of the water cylinder 14 are selected such that the projection value $p_R$ and the gradient s of the projection value profile 13 at the edge 8 correspond to the projection value and gradient of an extrapolated projection value profile 15, resulting from the parallel projection of the water cylinder 14 onto the extended detector surface 10.

Extrapolation values 16 can then be defined based on the water cylinder 15.

The height of the water cylinder 14 is selected to be equal to the distance between the detector lines in the column direction. This means that the object 5 is continued in small disks.

As described in detail below, the extrapolation method according to the prior art is not suitable for suppressing truncation artifacts in an effective manner in every instance.

Figure 4:
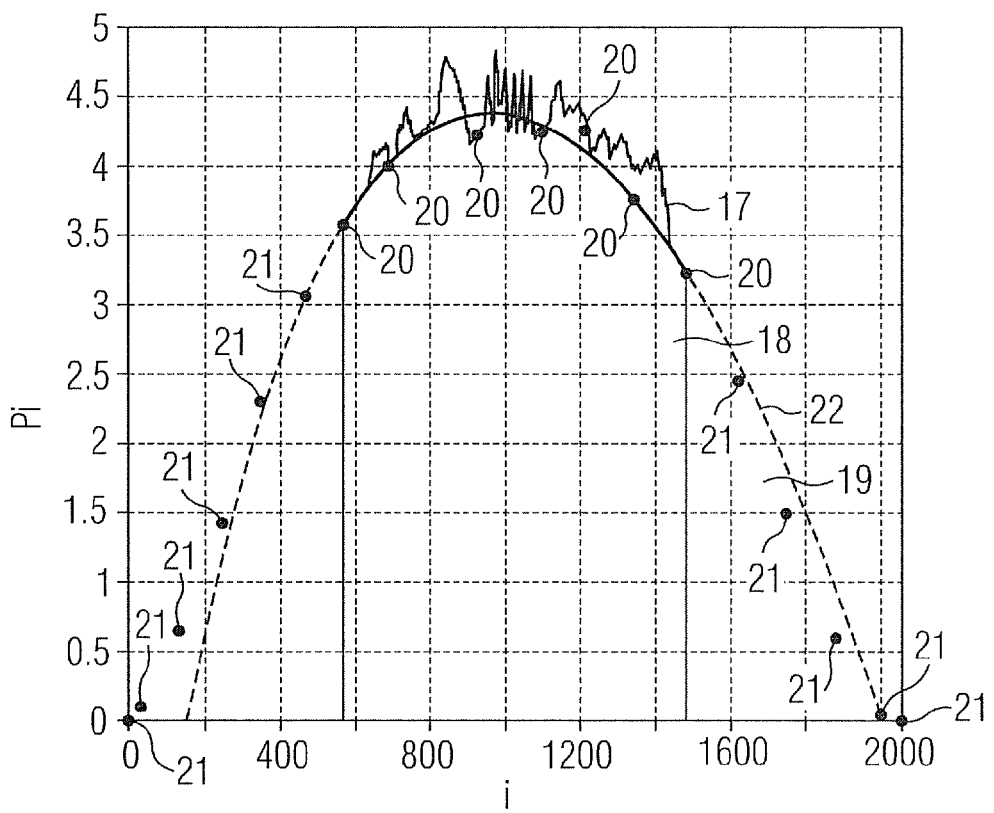
FIG. 4 shows a diagram of a correction method according to the invention.

FIG. 4 shows a diagram, in which a projection value profile 17 recorded by a detector line of the x-ray detector 4 is marked. In particular the projection values $p_i$ are shown against the column index i of the x-ray detector 4. An extrapolation described in more detail below causes the projection value profile 17, which extends along a line of the x-ray detector 4 within a projection image 18, to be extrapolated to external regions 19 outside the projection image 18.

The extrapolation is carried out as follows: The data line of the projection value profile 17 is first embedded into an elongated data line. Internal checkpoints 20 are then defined from the projection value profile 17 within the projection image 18. To define the internal checkpoints 20, the detector line is divided into a series of segments within the projection image 18. The local minima of the projection value profile 17 are then defined respectively within the segments. In FIG. 4 the projection value profile 17 is for example divided into seven segments. Selecting local minima segment by segment allows image points having low resolution compared with adjacent image points to be selected, which generally contain little structural information. The local minima thus found can then be subjected to a smoothing method, which suppresses noise effects and can further reduce the influence of the mapped structures on the result of the extrapolation. The smoothing method transfers the local minima to the internal checkpoints 20.

Selecting local minima and the subsequent smoothing prevent the extrapolation in the regions 19 outside the projection image resulting in projection values that increase in an outward direction, which would further falsify the result of the sectional image reconstruction.

External checkpoints 21 are then defined based on the internal checkpoints 20. In this process linear extrapolation is carried out segment by segment. It is a secondary condition here that the extrapolated external checkpoints 21 decrease monotonously in an outward direction.

It is possible to proceed as follows here:

Let us consider the three outermost internal checkpoints 20 with the projection values $p_{-2}$, $p_{-1}$ and $p_0$. The gradients of connecting straight lines between the three last internal checkpoints 20 with the projection values $p_{-2}$, $p_{-1}$ and $p_0$ have gradients, shown as $m_{-1}$ and $m_0$. A new gradient value $m_k$ of a connecting straight line between the outermost internal checkpoint 20 and the innermost external checkpoint 21 can then be determined as follows:

$$m_k = am_{k-1} + bm_{k-2}, k \geq 1$$

where a and b should be selected such that the external checkpoints 21 have projection values that decrease in an outward direction. This can be achieved for example by selecting $a=2$ and $b=-1$.

The projection values $p_k$ of the outer checkpoints 21 are then given by:

$$p_k = m_k \Delta + p_{k-1}, k \geq 1$$

where $\Delta$ is the column distance between $p_{-1}$ and $p_0$.

The associated column coordinates are $i_k = i_0 - k\Delta$ for left-side and $i_k = i_0 + k\Delta$ for right-side extrapolation, where $i_0$ is the column coordinate of the respectively outermost internal checkpoint 20 with the projection value $p_0$.

The extrapolation is continued correspondingly for the other external checkpoints 21.

Determination of the outer checkpoints 21 is terminated, when the new column coordinate lies outside the permissible value range for the column coordinate. In the case of left-side extrapolation the minimum value still within the value range is assigned to the column coordinate. In the case of right-side extrapolation the maximum coordinate value still within the value range is assigned to the column coordinate.

Determination of the outer checkpoints 21 is also terminated, when the projection value $p_k$ of the new external checkpoint 21 becomes negative. The new checkpoint value $p_k=0$ is then set.

To establish a smooth transition between the internal checkpoints 20 and the external checkpoints 21, the external checkpoints 21 can be weighted with a profile function. The profile function used can for example be the square of a sinusoidal function. Weighting with such a profile function also allows the monotonous decrease in the projection values of the external checkpoints 21 to be forced.

It can also be ensured that the gradients of the connecting straight lines between the external checkpoints 21 decrease in an outward direction, such that the projection values of the external checkpoints 21 run out gently in an outward direction.

In a further method step intermediate values are finally defined between the external checkpoints 21, being assigned to the individual columns.

To this end a parameterizable adaptation function 22 can on the one hand be tailored to the internal checkpoints 20 and the external checkpoints 21, decreasing monotonously to zero in an outward direction. Second order curves, known as conic section curves, have proven particularly suitable. The tailoring of elliptical segments generally produces good results for the reconstruction of sectional images. The tailored parameterizable function can then be used to calculate the intermediate values between the external checkpoints 21.

It is also possible to interpolate in a linear manner segment by segment between the outer checkpoints 21, in order to calculate the intermediate values between the outer checkpoints 21.

The fact that the extrapolation method described with reference to FIG. 4 results in significantly better suppression of truncation artifacts than the prior art becomes clear, in particular with reference to FIGS. 5 to 10.

Figure 5:
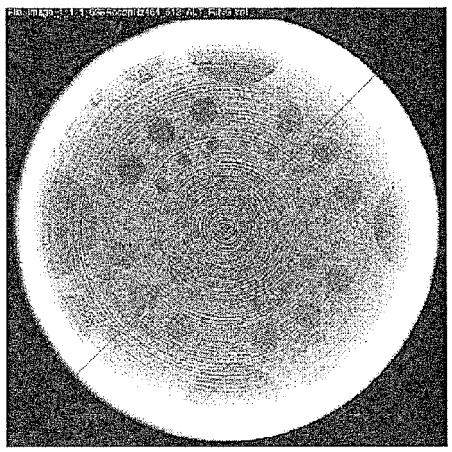
FIGS. 5 and 6 respectively show reconstructions of a medium contrast layer of the phantom body from FIG. 2 with the aid of the method according to the prior art and the method according to the invention.
Figure 6:
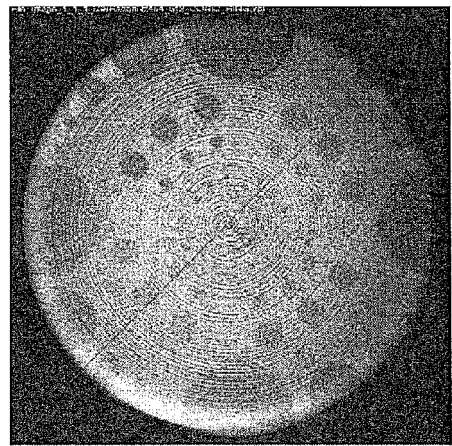

FIG. 5 shows the reconstructed truncated medium contrast layer of the phantom body 11 from FIG. 2 when using the extrapolation method according to FIG. 3. The excessive increase in the projection values in the peripheral regions of the sectional image is clearly shown. In contrast, in the sectional image in FIG. 6 the phantom body 11 was reconstructed using the extrapolation method described with reference to FIG. 4. FIG. 6 clearly shows the outlines of the inserts 12 in the peripheral regions of the projection image too.

Figure 7:
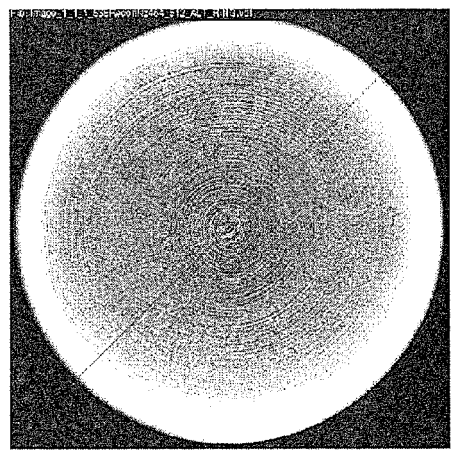
FIGS. 7 and 8 respectively show reconstructions of a low contrast layer of the phantom body from FIG. 2 with the aid of the method according to the prior art and the method according to the invention.
Figure 8:
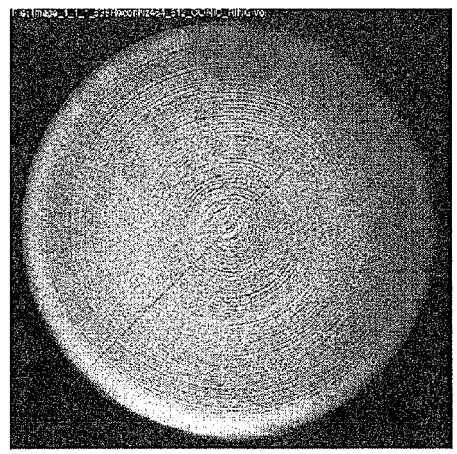

There are clear differences in the low contrast region too. FIG. 7 shows the reconstruction of a truncated low contrast layer of the phantom body 11 when the extrapolation method from FIG. 3 is used. Again the peripheral regions of the reconstructed sectional image show a significant excessive increase here. In contrast, in the sectional image shown in FIG. 8, produced using the extrapolation method shown in FIG. 4, there are no identifiable excessive increases in the peripheral regions.

An overview of FIGS. 5 to 8 also shows that, when the conventional method shown in FIG. 3 is used, the image values of the sectional image are reduced in the region of the isocenter.

Figure 9:
FIGS. 9 and 10 respectively show reconstructions of a truncated skull recording of a patient according to the prior art and the method according to the invention.
Figure 10:

This is shown clearly in FIGS. 9 and 10, which contain sectional images with identical windowing. FIG. 9 shows a truncated sectional image through the skull of a patient, produced using the conventional extrapolation method shown in FIG. 3. No further details can be identified in the region of the brain mass in FIG. 9.

These details can only be identified in FIG. 9 when the center of the window is scanned. This shows that image values that are too low have been reconstructed in the center of the image due to the truncation artifacts.

In contrast, in the sectional image shown in FIG. 10, produced using the method shown in FIG. 4, details can also be identified in the region of the brain mass, indicating a cerebral hemorrhage.

Since with the method described with reference to FIG. 4 it is not necessary to convert from fan beam to parallel beam data, the computation outlay is kept within limits. The method shown in FIG. 4 can therefore also be used with computed tomography with C-arm systems.

The adaptation function 22 tailored to the internal checkpoints 20 and the external checkpoints 21 is defined by the low-frequency components of the projection value profile 17. The local peripheral response of the projection value profile 17 therefore only influences the pattern of the adaptation function 22 to a minor degree. With the method described here it is therefore very unlikely that the local response of the projection value profile 17 will result in an incorrect extrapolation in the peripheral region, resulting in sectional images affected by truncation artifacts.

The invention claimed is:

1. A method for correcting a truncation artifact in a tomography examination method, comprising:

emitting a radiation to an object to be examined by a radiation source;
irradiating the object with the radiation in a projection direction;
detecting the radiation penetrating the object by a detector;
recording a project image by the detector from the detected radiation;
comparing a level of radiation attenuation in a point with a level of radiation attenuation in an adjacent point in an inner region within the projection image;
selecting an internal checkpoint having a lower level of radiation attenuation from the comparison;
extrapolating the projection image as a function of the selected checkpoint;
extending the projection image by the extrapolation; and
using the project image in a humanly perceptible manner.

2. A method for correcting a truncation artifact in a tomography examination method, comprising:
emitting a radiation to an object to be examined by a radiation source;
irradiating the object with the radiation in a projection direction;
detecting the radiation penetrating the object by a detector;
recording a project image by the detector from the detected radiation;
comparing a level of radiation attenuation in a point with a level of radiation attenuation in an adjacent point in an inner region within the projection image;
selecting an internal checkpoint having a lower level of radiation attenuation from the comparison;
extrapolating the projection image as a function of the selected checkpoint;
extending the projection image by the extrapolation; and
using the project image in a humanly perceptible manner,
wherein the projection image is divided into a plurality of segments and a plurality of internal checkpoints are selected respectively having local minimum levels of radiation attenuation in the segments.

3. The method as claimed in claim 2, wherein the internal checkpoint comprises a local minimum level of radiation attenuation.

4. The method as claimed in claim 2, wherein a smoothing method is performed in the internal checkpoints and a sliding mean value of the internal checkpoints is defined in the smoothing method.

5. The method as claimed in claim 2, wherein the internal checkpoint is extrapolated to an external checkpoint in an outer region outside the projection image having a projection value that decreases monotonously in an outward direction.

6. The method as claimed in claim 5, wherein the external checkpoint is weighted with a monotonously decreasing profile function and the monotonously decreasing profile function decreases to zero in the outward direction.

7. The method as claimed in claim 5, wherein an adaptation function is tailored to the internal checkpoint and the external checkpoint and the adaptation function is a conic section curve or an elliptical segment.

8. The method as claimed in claim 5, wherein a linear interpolation is performed segment by segment in the outer region outside the projection image.

9. The method as claimed in claim 2, wherein the detector is a digital detector with a plurality of detector elements and the projection image is extrapolated along a row of the detector elements.

10. The method as claimed in claim 2, wherein the radiation source is an x-ray radiation source and the detector is an x-ray detector.

11. A device for correcting a truncation artifact in a tomography examination method, comprising:
a radiation source that emits a radiation to an object to be examined;
a detector that records a projection image of the object by detecting the radiation; and
a calculation device that:
compares a level of radiation attenuation in a point with a level of radiation attenuation in an adjacent point in an inner region within the projection image,
selects an internal checkpoint having a lower level of radiation attenuation from the comparison,
extrapolates the projection image as a function of the selected checkpoint, and
extends the projection image by the extrapolation,
wherein the projection image is divided into a plurality of segments and a plurality of internal checkpoints are selected respectively having local minimum levels of radiation attenuation in the segments.

12. The device as claimed in the claim 11, wherein the internal checkpoint comprises a local minimum level of radiation attenuation.

13. The device as claimed in the claim 11, wherein a smoothing method is performed in the internal checkpoints and a sliding mean value of the internal checkpoints is defined in the smoothing method.

14. The device as claimed in the claim 11, wherein the internal checkpoint is extrapolated to an external checkpoint in an outer region outside the projection image having a projection value that decreases monotonously in an outward direction.

15. The device as claimed in the claim 14, wherein the external checkpoint is weighted with a monotonously decreasing profile function and the monotonously decreasing profile function decreases to zero in the outward direction.

16. The device as claimed in the claim 14, wherein an adaptation function is tailored to the internal checkpoint and the external checkpoint and the adaptation function is a conic section curve or an elliptical segment.

17. The device as claimed in the claim 14, wherein a linear interpolation is performed segment by segment in the outer region outside the projection image.

18. The device as claimed in the claim 11, wherein the detector is a digital detector with a plurality of detector elements and the projection image is extrapolated along a row of the detector elements.

19. The device as claimed in the claim 11, wherein the radiation source is an x-ray radiation source and the detector is an x-ray detector.

* * * * *